United States Patent
Lopatin et al.

(10) Patent No.: US 7,530,268 B2
(45) Date of Patent: May 12, 2009

(54) DEVICE FOR DETERMINING AND/OR MONITORING AT LEAST ONE PHYSICAL OR CHEMICAL PROCESS VARIABLE OF A MEDIUM IN A CONTAINER

(75) Inventors: Sergej Lopatin, Lörrach (DE); Helmut Pfeiffer, Steinen (DE)

(73) Assignee: Endress + Hauser GmbH + Co. KG, Maulburg (DE)

( * ) Notice: Subject to any disclaimer, the term of this patent is extended or adjusted under 35 U.S.C. 154(b) by 160 days.

(21) Appl. No.: 10/554,199

(22) PCT Filed: Apr. 21, 2004

(86) PCT No.: PCT/EP2004/004183

§ 371 (c)(1),
(2), (4) Date: Oct. 3, 2006

(87) PCT Pub. No.: WO2004/094964

PCT Pub. Date: Nov. 4, 2004

(65) Prior Publication Data

US 2007/0028691 A1    Feb. 8, 2007

(30) Foreign Application Priority Data

Apr. 24, 2003   (DE)   ................................ 103 18 705

(51) Int. Cl.
G01N 29/02      (2006.01)
G01F 23/28      (2006.01)
G01N 9/34       (2006.01)
(52) U.S. Cl. .................. 73/290 V; 73/290 B; 73/19.03; 73/24.06; 73/32 A; 73/54.24; 340/621

(58) Field of Classification Search ............... 73/290 V, 73/290 R
See application file for complete search history.

(56) References Cited

U.S. PATENT DOCUMENTS

| | | | | |
|---|---|---|---|---|
| 4,499,765 | A | * | 2/1985 | Benz et al. ................. 73/290 V |
| 4,740,726 | A | * | 4/1988 | Umezawa .............. 310/316.01 |
| 4,920,787 | A | * | 5/1990 | Dual et al. .................. 73/54.41 |
| 5,247,832 | A | * | 9/1993 | Umezawa et al. ......... 73/290 V |

(Continued)

FOREIGN PATENT DOCUMENTS

DE           3734077           4/1989

(Continued)

*Primary Examiner*—Hezron Williams
*Assistant Examiner*—Rose M Miller
(74) *Attorney, Agent, or Firm*—Bacon & Thomas, PLLC

(57) ABSTRACT

An apparatus for determining and/or monitoring at least one physical or chemical, process variable of a medium and includes at least one mechanically oscillatable unit and at least one driving/receiving unit. The mechanically oscillatable unit includes a tube and an internal oscillator. The tube is connected to a securement unit with an end turned away from the process and the end of the tube turned toward the process is embodied as a free end. The tube surrounds the internal oscillator and the internal oscillator is secured to the end of the tube turned toward the process with an end turned toward the process. The driving/receiving unit excites the mechanically oscillatable unit to oscillate, respectively it receives the oscillations of the mechanically oscillatable unit. The internal oscillator has at least one groove/neck, which determines at least the oscillation frequency of the mechanically oscillatable unit.

11 Claims, 3 Drawing Sheets

U.S. PATENT DOCUMENTS

| | | | |
|---|---|---|---|
| 5,670,709 A * | 9/1997 | Gallagher | 73/54.24 |
| 5,969,621 A * | 10/1999 | Getman et al. | 340/621 |
| 6,105,425 A * | 8/2000 | Kawakatsu | 73/290 V |
| 6,205,855 B1 * | 3/2001 | Pfeiffer | 73/290 V |

FOREIGN PATENT DOCUMENTS

| | | |
|---|---|---|
| DE | 3912038 | 10/1990 |
| DE | 3883168 T | 2/1994 |
| DE | 10260088 | 8/2004 |
| EP | 0 499265 | 8/1992 |
| EP | 0 875739 | 11/1998 |
| WO | WO 9414047 | 6/1994 |

* cited by examiner

DEVICE FOR DETERMINING AND/OR MONITORING AT LEAST ONE PHYSICAL OR CHEMICAL PROCESS VARIABLE OF A MEDIUM IN A CONTAINER

FIELD OF THE INVENTION

The invention relates to an apparatus for determining and/or monitoring at least one physical or chemical, process variable of a medium and includes at least one mechanically oscillatable unit having a tube and an internal oscillator, with the tube being connected with a securement unit at an end turned away from the process, with the end of the tube facing toward the process being in the form of a free end, with the tube surrounding the internal oscillator, and with the internal oscillator being secured, at an end facing toward the process, to the end of the tube facing toward the process, and further including at least one driving/receiving unit, with the driving/receiving unit exciting the mechanically oscillatable unit to oscillate, respectively with the driving/receiving unit receiving the oscillations of the mechanically oscillatable unit. Examples of process variables are the fill level, viscosity or density of a medium. The medium can, in such case, be a liquid or a bulk good.

BACKGROUND OF THE INVENTION

Patent DE 692 02 354 T2 describes a vibration-type level sensor. A registering, tube unit is secured with one end as fixed end at a securement unit and sealed at another end with an end cap. Secured to this end cap and in the tube unit is an internal, vibration part. The vibration part has an elongated, rectangular, rod shape. Secured to a side surface of this vibration part is a vibrating mechanism. The registering tube, the end cap and the internal vibration part together form a folded cantilever. Attached in the end cap is a registering mechanism, which registers the changes of the vibrating of the folded cantilever. According to the patent, the length ratio between the length of the tube and the length of the vibration part should lie between 1.6 and 3.0, in order to have an optimum possible output voltage from the registering unit. If the tube unit is secured to the securement unit via a membrane, or diaphragm, then a vibration node of the folded cantilever can be moved to the securement unit. This makes it possible to use a shorter length for the tube unit. With a membrane, or diaphragm, the length ratio between the length of the tube and the length of the vibration unit should lie between 1.0 and 2.5. A disadvantage of this folded cantilever is that the length of the sensor is very large. This is a consequence of the fact that the oscillation frequency of the folded cantilever is determined by the mass and by the length of the inner vibration part. In order to reduce the oscillation frequency, the internal vibration part must be as long as possible. Such a reduction of the oscillation frequency has the general advantage that larger amplitudes can be achieved therewith and that the sensor therefore possesses a broader range of application. Along with the long internal vibration part, in most cases, a still greater tube length is required. This length ratio prevents that oscillation energy is transferred from the folded cantilever to the container. On the basis of these considerations, a large length of the sensor results. The membrane on the securement unit represents a possibility for shortening the length. One can perceive from Patent DE 37 40 598 C2, however, that mechanical manufacturing tolerances result in the fact that the oscillation node does not act exactly on the membrane securement. As a consequence, also here energy losses can occur. Moreover, the constraint, that oscillation nodes of such a membrane be located at the membrane securement, limits the choice of oscillation frequencies. A further disadvantage of Patent DE 692 02 354 T2 is that the internal oscillation part requires a special geometry, which is associated with the positioning and structure of the vibrating mechanism. Additionally, besides the vibrating mechanism for the excitement, also a registering mechanism for receiving is required.

SUMMARY OF THE INVENTION

An object of the invention is to determine and/or monitor a physical or chemical process variable of a medium using a mechanically oscillatable unit and a driving/receiving unit, wherein the accuracy of measurement is as great as possible.

The object is solved according to the invention by providing the internal oscillator with at least one groove/neck, which determines the oscillation frequency of the mechanically oscillatable unit.

Essentially, the oscillation frequency depends on the mass moment of inertia of the internal oscillator relative to the axis of rotation in the groove/neck. Further dependencies result from the bending stiffness of the section of the internal oscillator with groove/neck and from the mass moment of inertia of the tube relative to the axis of rotation in the fixed support of the securement unit. Slightly also participating in determination of the oscillation frequency is the rotational stiffness of the region of the securement unit, where the tube is secured. For example, the rotational stiffness for the internal oscillator is defined by the diameter and/or the length of the groove or neck. Depending on the embodiment, also the mass of the internal oscillator enters in. This is, in certain cases, to be considered in the further development of the internal oscillator. Since the rotational stiffness, among other things, contributes to the determining of the oscillation frequency, the working frequency can be suitably tuned via the structure and/or the position of the groove/neck. Thus, the oscillation frequency can be reduced via the dimensioning and/or the positioning of the groove or neck, this, in turn, leading to an increase in the amplitude of the oscillation. For the further, finer determining of the oscillation frequency, or amplitude, the further development of the structure is relevant, as already indicated above. In the case of the variant involving the groove, there is the advantage that the internal oscillator is structured as a rotary part, this leading to cost savings. The groove or neck is preferably embodied rotationally symmetrically, so that, among other things, no eccentricities arise. Furthermore, it should also be heeded that the internal oscillator still be stable, despite the groove/neck, such that the oscillation not lead to plastic deformation or the like.

An advantageous embodiment provides that the groove/neck is located in the direction of the end of the internal oscillator facing toward the process. The groove/neck is thus optimally located in the transition between the tube and the internal oscillator. In this way, the inertial mass of the internal oscillator is greatest above the groove/neck. Furthermore, this is the point, on which the forces act and where thus also the rotational stiffness makes itself felt. The positioning of the groove/neck depends, however, also on the position and structure of the driving/receiving unit, in order that the driving/receiving unit can act optimally, or receive optimally, as the case may be, or so that, as much as possible, no destructive forces and moments act on the internal oscillator.

During the oscillatory movement, the oscillating parts (tube and internal oscillator) transmit forces and torques, which are absorbed by the securement unit as reaction forces and moments. The securement unit, or base unit, is directly, or, in certain cases, by way of a further element, connected with the container, in which the medium is located. For preventing coupling to the container and, thus, possible energy loss, care must be taken, that the mechanically oscillatable unit is in energy equilibrium. This means that the sums of the forces and torques, which are produced by the individual components during the oscillatory movement, are essentially zero in the securement unit.

An advantageous embodiment includes that an additional weight is provided in the securement unit. With this embodiment, the mechanically oscillatable unit is essentially decoupled from the securement unit with reference to a transmission of oscillation energy. Additionally, the weight also has the advantage of making the securement stabler for oscillation.

Advantageous embodiments provide that the tube and/or the internal oscillator have/has a round, elliptical, square or polygonal cross section. Thus, for the geometry, there are scarcely any specifications or limits. A round cross section for the tube has the advantage that the danger is reduced that the mechanically oscillatable unit experiences bending. This also makes possible an installation at any place in the container of the medium. Moreover, a round cross section makes manufacture simple and saves costs associated therewith.

Advantageous embodiments provide that the internal oscillator is hollow, solid, or partially hollow and partially solid. It should be assured that the inner oscillator, despite the groove, or neck, is stable enough in this region, i.e. it must not be caused to break by the oscillations. Since, for the internal oscillator, mass plays an important role, it makes sense to construct it using solid material. In the case of a hollow tube, the oscillation frequency would be increased. In this way, naturally, there is again an opportunity for tuning the oscillation frequency.

An advantageous embodiment includes that, in the driving/receiving unit, only a single piezo unit is provided, which serves both as driving unit and as receiving unit. Another embodiment includes that, in the driving/receiving unit, at least two piezo units are provided, with at least one piezo unit serving as driving unit and at least one piezo unit serving as receiving unit, with the piezo units being positioned at the same position. This enables marked simplification of the installation of the piezo unit and of the design of tube, internal oscillator and other possible affixing elements. This also simplifies the electrical connection of the piezo unit. Further advantages in the case of using only one unit lie in the lower manufacturing costs. A further advantage is that a module independent of the oscillator is produced and the module can be inspected and tested before installation, something which is always desired in production. The piezo units are usually clamped. In the case of such a piezo unit, it is also meaningful, among other things, for efficiency, that the internal oscillator be connected as much as possible with the entire surface of the piezo units, that, thus, e.g. the groove/neck not be located directly on the piezo unit, which has a much larger diameter. These and similar considerations for the embodiment are within the skill of the art and depend strongly on the nature and detailed conditions of the concrete implementation.

A quite specially advantageous embodiment includes that the piezo unit is a piezoelectric element comprised of at least two segments, which are polarized in mutually opposing directions, with the polarization directions lying parallel to an axis of rotation of the mechanically oscillatable unit. If a voltage is applied to the upper and lower sides of this piezo unit, then the one segment contracts and the other segment expands, i.e. the one segment has a lesser height and the other a greater height. This special piezo unit has, therefore, the great advantage that wagging movements, or rotating movements, can be directly produced, or detected, as the case may be.

An embodiment provides that the driving/receiving unit is positioned between the end of the internal oscillator turned toward the process and the end of the tube turned toward the process. This positioning, in connection with the specially embodied piezo unit, serves to assure that the mechanically oscillatable unit is excited to direct wagging movements, or to rotational movements, or that the oscillations, which involve such movements, are received, as the case may be. Further advantages are that components are involved, which are easily assembled, that a direct and rigid coupling with the oscillator is produced, and that axial movements, e.g. disturbances, are due to the different polarization directions of the piezo unit, not received. Furthermore, this is a cost-favorable solution, since fewer components are required.

An embodiment provides that the internal oscillator exhibits at least a second grove/neck. Associated with this is an embodiment, which includes that the driving/receiving unit is positioned between the first groove/neck and the second groove/neck. The first groove/neck is located, in such case, very near to the end cap, thus on the end of the end of the internal oscillator, and also of the tube, turned toward the process. The driving/receiving unit is located also as near as possible to this end, or near to the affixing of the internal oscillator, so that an optimal utilization of the oscillation energy can occur. For obtaining the direct wagging movements, the piezo unit with the oppositely directed polarizations is also very effective. This construction increases the measurement sensitivity of the sensor.

BRIEF DESCRIPTION OF THE DRAWINGS

The invention will now be explained in greater detail on the basis of the drawings, the figures of which show as follows.

DESCRIPTION OF THE PREFERRED EMBODIMENTS

Figure 1:
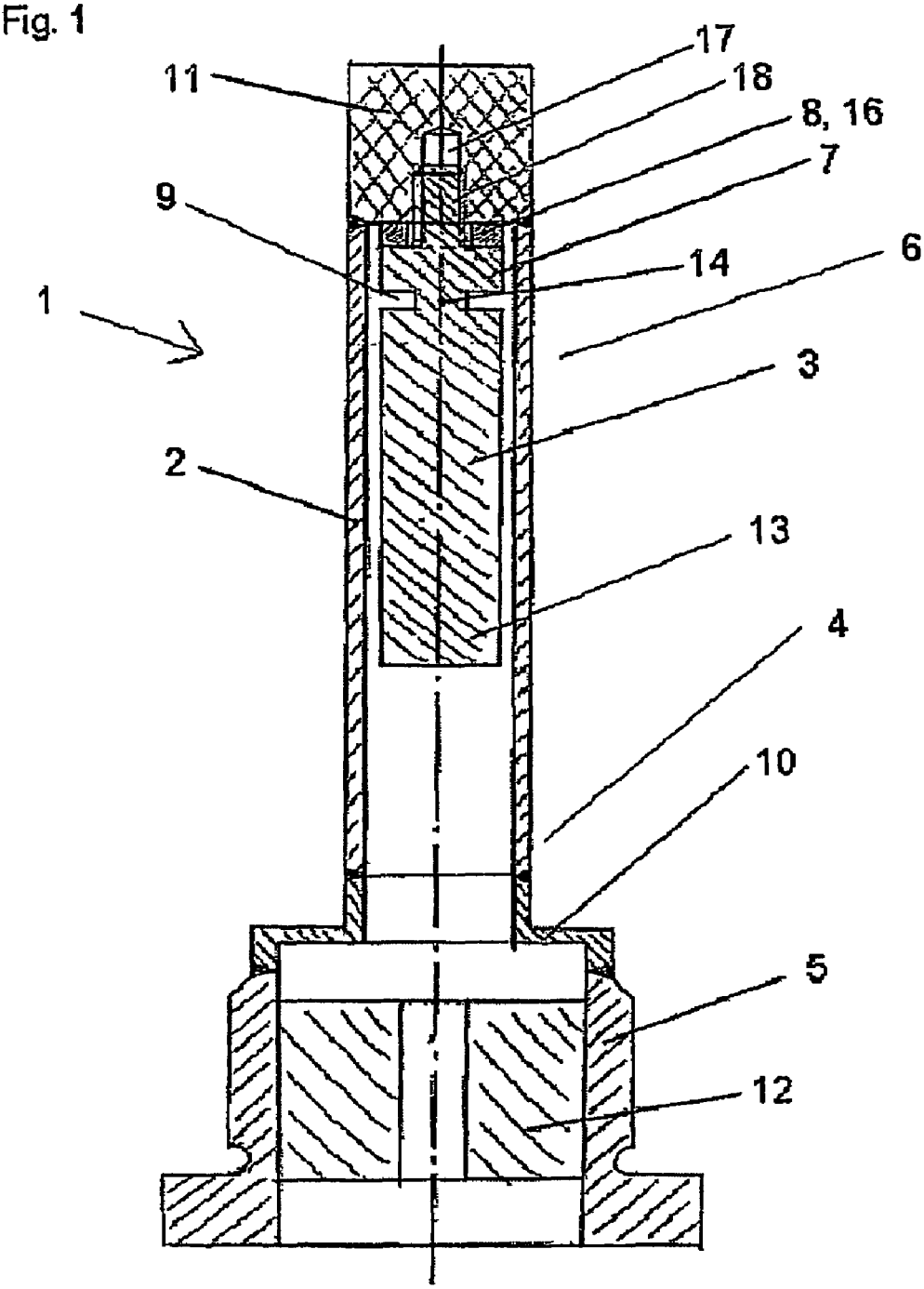
FIG. 1 a cross section through one implementation of the apparatus.

FIG. 1 shows a cross section through an implementation of the apparatus. The mechanically oscillatable unit 1 includes a tube 2 and an internal oscillator 3. The tube 2 has two ends, end 6 being turned toward the process, and end 4 being turned away from the process. With the end 4 turned away from the process, tube 2 is secured to a securement unit 5. In the instance illustrated here, the end 4 turned away from the process is secured in a screw-in piece 10. The screw-in piece 10 can also be a membrane, or diaphragm, in the securement unit 5. The embodiment of membrane 10 determines, in such case, among other things, also the oscillation frequency of the mechanically oscillatable unit 1. A membrane is present, when the diameter of a securement disk is very much greater than its thickness. Or, for a ring membrane, the difference between the outer diameter and the inner diameter is very much greater that the thickness of the membrane. The oscillation frequency of the mechanically oscillatable unit 1 decreases with decreasing membrane thickness. Simultaneously, however, the amplitude of the oscillation of the mechanically oscillatable unit 1 also decreases. Additionally in this embodiment, also an additional weight 12 is provided in the securement unit 5. Weight 12, on the one hand, makes the securement unit 5 stabler, and, on the other hand, contributes to the decoupling of the oscillatable unit 1 from the securement unit 5. Secured to the end 6 of the tube 2 facing toward the process is an end cap 11. In end cap 11 is a bore 17, in which the securement element 18 of the end 7 of the internal oscillator 3 facing toward the process is inserted for the connecting of the internal oscillator 3 with the tube 2. Such a screwed connection 17, 18 makes it possible e.g. to affix the internal oscillator easily and with less complications, also in the case of a very long tube 2, on the end 6 of the tube 2 facing toward the process. A longer tube 2 could be required for special media or for special containers. For the screw-in operation, it is also helpful to provide a slot in the end 13 of the internal oscillator 3 turned away from the process, so that e.g. a screwdriver can be used to aid in accomplishing the connection (see also FIG. 3 in this regard). The driving/receiving unit 8, which excites the mechanically oscillatable unit 1 to oscillate, respectively receives the oscillations of the mechanically oscillatable unit 1, is secured between the inner oscillator 3 and the end cap 11 on the tube 2 in the example of an embodiment. Due to the securement of the inner oscillator 3 via the securement element 18, the driving/receiving unit is provided in this case in the form of a ring. The driving/receiving unit 8 is preferably at least one piezo unit 16. If different piezo units 16 are provided for the driving and receiving, then this plurality of piezo units 16 is located in the same position, e.g. in the form of a stack. A piezoelectric unit with two mutually opposing polarizations can, in this position, produce direct wagging oscillations.

The inner oscillator 3 is, in the illustrated case, a solid, round rod. Other shapes are, however, also possible. Oscillator 3 has a groove 9 in the direction of end 7 turned toward the process. A neck would likewise be a suitable embodiment. The groove/neck 9 is rotationally symmetric as provided here. Other embodiments are within the ability of those skilled in the art. Especially the diameter and the length of groove 9 determine the rotational stiffness $C_i$ of this section of the internal oscillator 3 in this groove region. The resonance frequency of the internal oscillator 3 is, in turn, determined by this rotational stiffness $C_i$ and the mass moment of inertia i of the internal oscillator. Thus, the dimensioning of the groove 9 has direct effects on the resonance frequency of the internal oscillator 3. The oscillation frequency of the mechanically oscillatable unit 1 corresponds to the resonance frequency of the internal oscillator 3 in the state in which it is coupled with tube 2. Additionally, this oscillation frequency is influenced by the mass moment of inertia of the tube 2 and its bending stiffness. This, however, is only slight, so long as the resonance frequency of the tube 2 is very much smaller than the resonance frequency of the internal oscillator 3. Thus, it is possible to use the groove 9 and/or its position to influence the oscillation frequency of the mechanically oscillatable unit 1.

A basic idea of the invention is thus that the oscillation frequency of the mechanically oscillatable unit 1 is adjustable by means of the groove/neck 9. A smaller oscillation frequency leads, for equal exciting energy, to a higher amplitude. This groove/neck thus enables that the internal oscillator 3 can be made shorter. Relevant variables with reference to the groove/neck 9 are, in such case, its structure (diameter, length) and its position on the internal oscillator 3.

Figure 2:
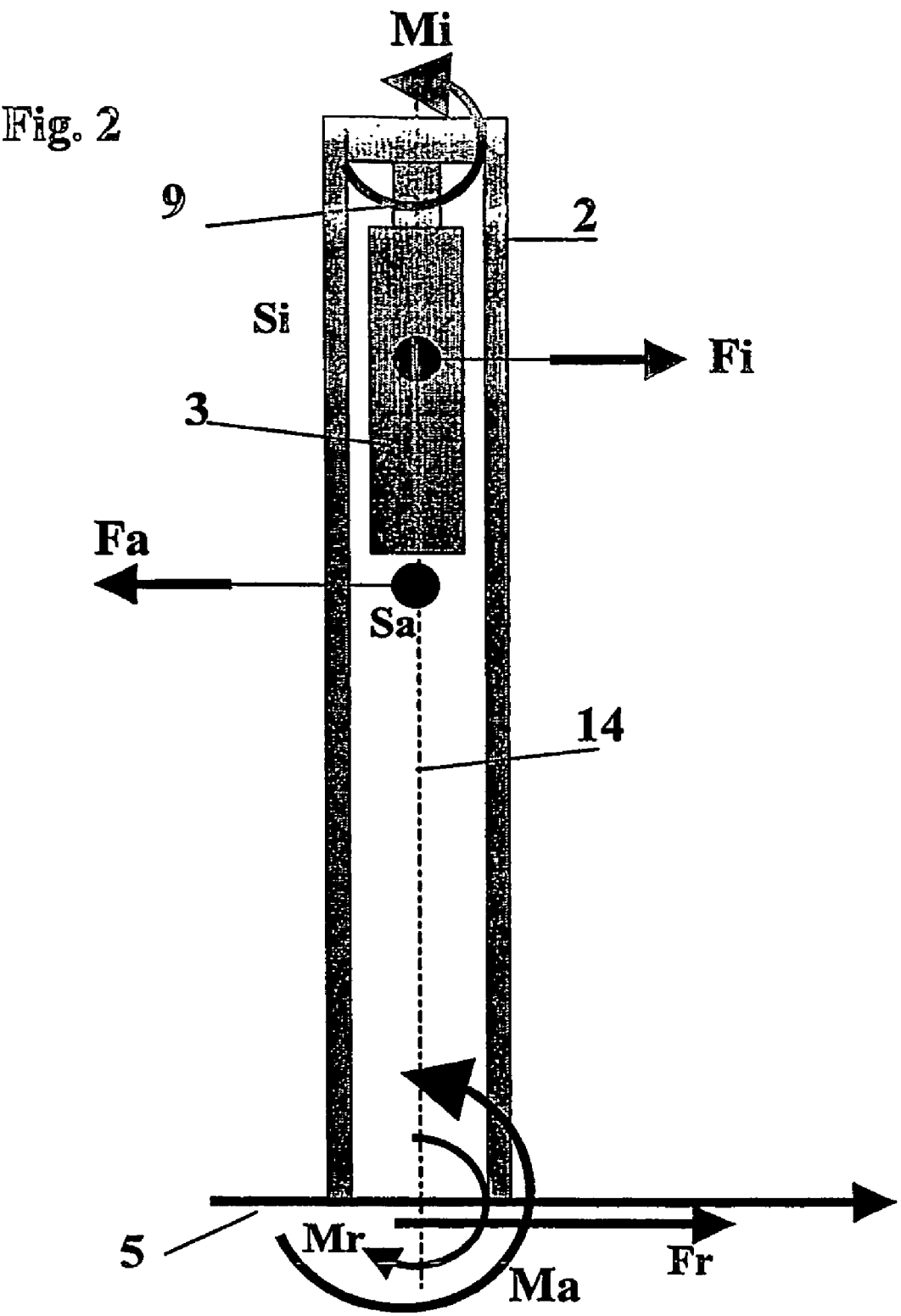
FIG. 2 a schematic illustration of the oscillations and the arising forces.

FIG. 2 details the acting and resulting forces and moments of FIG. 1. Therein, one can also see that the tube 2 and the internal oscillator 3 oscillate oppositely to one another. During the oscillatory movement, the oscillating parts 2, 3 transmit forces Fi, Fa and moments Mi and Ma, which are absorbed by the securing unit 5 as reaction forces Fr and moments Mr. In order to prevent a coupling to the container and resulting energy loss and disturbance by oscillations of the container, it is necessary to assure that the mechanically oscillatable unit 1 is in energetic equilibrium. This means that the sums of the forces and moments produced during the oscillatory movement must be zero in the securement unit 5. The requirements are that the forces Fi and Fa acting on the centers of gravity of the internal oscillator Si and of the tube 2 Sa must be of the same size: Fi=Fa. Likewise, the moments of the internal oscillator Mi and of the tube Ma must be equal: Mi=Ma. If these two conditions are approximately fulfilled, then only negligible forces Fr or moments Mr are transmitted to the securement unit 5 and essentially no energy loss from the mechanically oscillatable unit 1 occurs.

Figure 3:
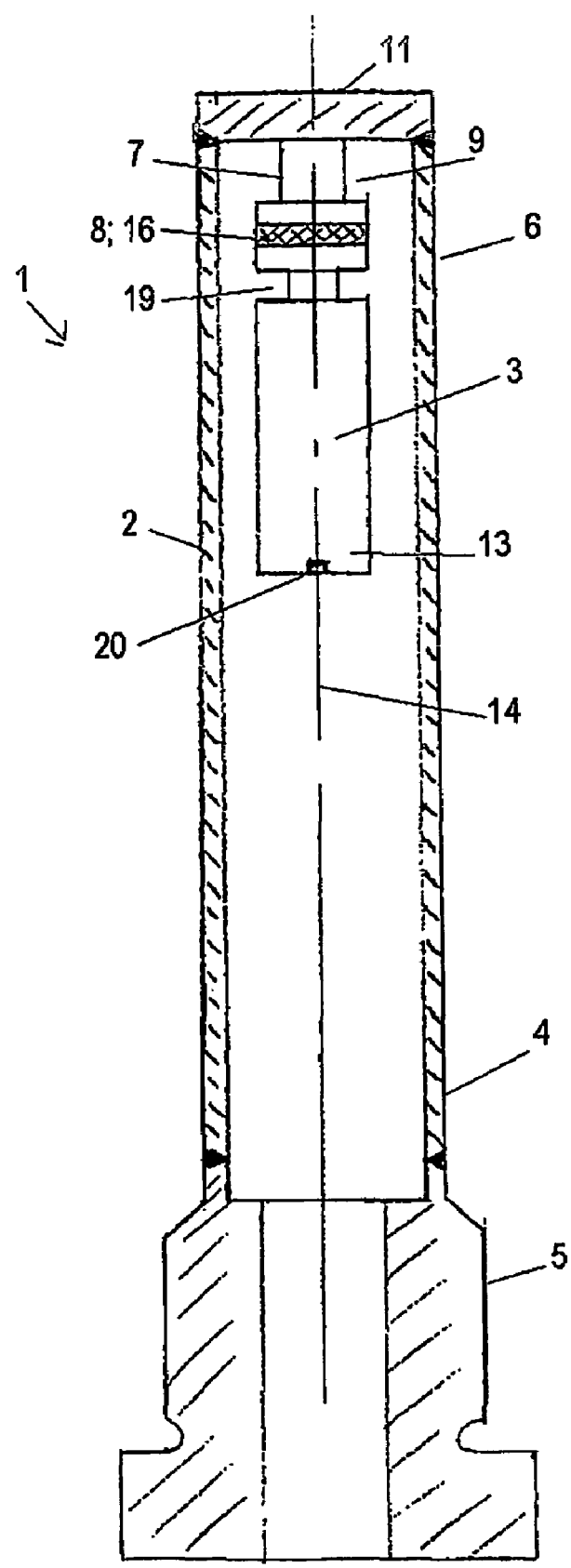
FIG. 3 a cross section through a further implementation of the apparatus.

FIG. 3 shows an embodiment in which the internal oscillator exhibits two necks 9 and 19. The driving/receiving unit 8, or, in this case, the piezo unit 16 with the two segments, whose polarizations are mutually opposed, is/are located between the two necks 9 and 19. Through the structure of the piezo unit 16, a voltage applied to the piezo unit 16 leads to a contracting of the one segment of the piezo unit 16, while the other segment expands. Thus, a wagging motion is directly produced, thus resulting in the oscillation. The securement unit 5 is, in this case, more solidly embodied as compared to the situation in FIG. 1, or, viewed differently, the added weight 12 is, here, a part of the securement unit 5 itself. Also, this illustration shows the slot 20 in the internal oscillator 3, via which the inner oscillator 3 can be screwed into the end cap 11 of the tube 2 using a screwdriver. This is also an example for how the mechanically oscillatable unit 1 can be embodied to be very simply assemblable, and thus cost favorable.

LIST OF REFERENCE CHARACTERS

1 mechanically oscillatable unit
2 tube
3 internal oscillator
4 tube end turned away from the process
5 securement unit
6 tube end turned toward the process
7 end of the internal oscillator turned toward the process
8 driving/receiving unit
9 groove/neck
10 screw-in piece
11 end cap
12 additional weight
13 end of the internal oscillator turned away from the process
14 axis of rotation
16 piezo unit
17 bore
18 affixing unit
19 second groove/neck
20 slot

The invention claimed is:

1. An apparatus for determining and/or monitoring at least one physical or chemical process variable of a medium, comprising:
   at least one mechanically oscillatable unit which includes a tube and an internal oscillator, said tube having a first end and a second end;
   a securement unit connected to said first end of said tube, said first end of said tube being turned away from the process, and said second end of said tube being turned toward the process and embodied as a free end, said tube surrounds said internal oscillator; and at least one driving/receiving unit, said driving/receiving unit excites said at least one mechanically oscillatable unit to oscillate, respectively, wherein:

said internal oscillator is secured to said free end of said tube by an end turned toward the process;

said driving/receiving unit receives the oscillations of said at least one mechanically oscillatable unit;

said internal oscillator has at least one groove/neck, which determines at least the oscillation frequency of said at least one mechanically oscillatable unit;

the resonance frequency of said tube is smaller than the resonance frequency of said internal oscillator; and as a result any effect by said tube on the oscillation frequency of said at least one mechanically oscillatable unit is negligible.

2. The apparatus as claimed in claim 1, wherein:
said groove/neck is located in the direction of the end of said internal oscillator turned toward the process.

3. The apparatus as claimed in claim 1, wherein:
an additional weight is provided in said securement unit.

4. The apparatus as claimed in claim 1, wherein:
said tube and/or said internal oscillator have/has one of: a round, elliptical, square and polygonal cross section.

5. The apparatus as claimed in claim 1, wherein:
said internal oscillator is one of: hollow, solid and partially hollow and partially solid.

6. The apparatus as claimed in claim 1, wherein:
only a single piezo unit in said at least one driving/receiving unit is provided, which serves as a driving, and as a receiving, unit.

7. The apparatus as claimed in claim 1, wherein:
at least two piezo units in said at least one driving/receiving unit are provided, with least one piezo unit serving as driving unit and at least one piezo unit serving as receiving unit, said at least tow piezo units being piezo units positioned at the same position.

8. The apparatus as claimed in claim 6, wherein:
said piezo unit is a piezoelectric element, which is composed of at least two segments, which are polarized in mutually opposite directions, said polarization directions lie parallel to an axis of rotation of said at least one mechanically oscillatable unit.

9. The apparatus as claimed in claim 1, wherein:
said at least one driving/receiving unit is positioned between end of said internal oscillator turned toward the process and the end of said tube turned toward the process.

10. The apparatus as claimed in claim 1, wherein:
said internal oscillator has at least a second groove/neck.

11. The apparatus as claimed in claim 10, wherein:
said at least one driving/receiving unit is positioned between said first groove/neck and said second groove/neck.

* * * * *